(12) United States Patent
Ko (10) Patent No.: US 8,951,566 B2
(45) Date of Patent: Feb. 10, 2015

(54) PROCESS FOR PREPARING PRODUCTS COMPRISING STABILISED ACTIVES AND COMPOSITIONS COMPRISING SAME

(76) Inventor: Sai Ying Ko, Beijing (CN)

( * ) Notice: Subject to any disclaimer, the term of this patent is extended or adjusted under 35 U.S.C. 154(b) by 0 days.

(21) Appl. No.: 13/320,520

(22) PCT Filed: Feb. 18, 2011

(86) PCT No.: PCT/AU2011/000173
§ 371 (c)(1),
(2), (4) Date: May 14, 2012

(87) PCT Pub. No.: WO2012/109694
PCT Pub. Date: Aug. 23, 2012

(65) Prior Publication Data
US 2012/0219624 A1    Aug. 30, 2012

(51) Int. Cl.
| | | |
|---|---|---|
| *A61K 9/14* | (2006.01) | |
| *A61K 9/16* | (2006.01) | |
| *A61K 9/28* | (2006.01) | |
| *B01J 13/00* | (2006.01) | |
| *B05D 3/00* | (2006.01) | |
| *B01J 13/04* | (2006.01) | |
| *A23K 1/00* | (2006.01) | |
| *A61K 38/18* | (2006.01) | |
| *A61K 38/19* | (2006.01) | |
| *A61K 38/20* | (2006.01) | |
| *A61K 38/21* | (2006.01) | |
| *A61K 38/27* | (2006.01) | |
| *A61K 9/20* | (2006.01) | |
| *A23P 1/04* | (2006.01) | |
| *A23L 1/00* | (2006.01) | |

(52) U.S. Cl.
CPC ............. *B01J 13/043* (2013.01); *A23K 1/004* (2013.01); *A61K 38/1816* (2013.01); *A61K 38/193* (2013.01); *A61K 38/20* (2013.01); *A61K 38/21* (2013.01); *A61K 38/27* (2013.01); *A61K 9/1676* (2013.01); *A61K 9/2081* (2013.01); *A23P 1/04* (2013.01); *A23L 1/0029* (2013.01)
USPC ........................... 424/490; 424/489; 427/2.14

(58) Field of Classification Search
None
See application file for complete search history.

(56) References Cited

U.S. PATENT DOCUMENTS

| | | | |
|---|---|---|---|
| 3,771,237 A | 11/1973 | Hansen et al. | |
| 5,601,760 A | 2/1997 | Rosenberg | |
| 6,974,594 B2 * | 12/2005 | Ko et al. | 424/493 |
| 7,011,847 B2 * | 3/2006 | Lulla et al. | 424/458 |
| 2007/0077308 A1 | 4/2007 | Giner | |
| 2009/0238885 A1 | 9/2009 | Alting et al. | |

FOREIGN PATENT DOCUMENTS

| | | |
|---|---|---|
| SU | 1720678 A1 | 3/1992 |
| WO | 2009070011 A1 | 6/2009 |

OTHER PUBLICATIONS

Australian Patent Office, International Search Report and Written Opinion for PCT/AU2011/000173, Mar. 31, 2011.

\* cited by examiner

*Primary Examiner* — Carlos Azpuru
*Assistant Examiner* — Casey Hagopian
(74) *Attorney, Agent, or Firm* — Perkins Coie LLP (57) ABSTRACT

The present invention broadly relates to a process for preparing products comprising active components, and in particular biological materials, wherein the active components are stabilized. The invention further relates to compositions comprising the products, and in particular compositions comprising therapeutic biological materials.

28 Claims, 2 Drawing Sheets

PROCESS FOR PREPARING PRODUCTS COMPRISING STABILISED ACTIVES AND COMPOSITIONS COMPRISING SAME

TECHNICAL FIELD

The present invention broadly relates to a process for preparing products comprising active components, and in particular biological materials, wherein the active components are stabilised. The invention further relates to compositions comprising the products, and in particular compositions comprising therapeutic biological materials.

BACKGROUND OF THE INVENTION

Many biological materials, such as proteins and whole cells, which are useful for the treatment and prevention of human and animal diseases or as food supplements have a limited shelf life. The limited shelf life is considered to be the result of protein instability at storage temperature. Whilst the shelf life of some proteins and cell cultures may be extended by storing them at low temperature (i.e. 4° C. to 8° C.), shelf lives of less than eighteen months are common.

Biologically active proteins are generally folded in a complex three dimensional manner which is unique to each protein. The proteins are generally organised on three levels; having a primary structure, consisting of a linear chain of covalently bonded amino acid residues (a peptide chain); a secondary structure, in which the peptide chain folds into regular patterns (such as, α helices and β-pleated sheets); and a tertiary structure in which the folded chain further folds upon itself to form a compact structure. In addition, some proteins consist of more than one polypeptide chain held in close arrangement to form what is referred to as the quaternary structure. It is the tertiary and/or the quaternary structure that dictates a protein's ultimate biological activity.

The ultimate structure of a protein may be effected by a number of environmental factors, for example temperature, pH, the presence or absence of certain co-factors or metals, the presence of oxygen, enzymes, oxidising or reducing agents and the presence of water or moisture. Where conditions are not optimal, a protein may not form properly or may denature, such that its biological function is lost, or is at least diminished.

The cells of animals, plants and microorganisms may be considered complex protein materials in the broadest sense as they contain numerous proteins enclosed by a cell membrane and/or cell wall, which membrane or wall inturn presents additional proteins at the cell's surface. As with proteins, the viability of a cell is dependent on the environment in which it resides; for example, temperature, pH, the presence or absence of certain co-factors or metals, presence or absence of certain nutrients, metabolic waste, oxygen, enzymes, oxidising or reducing agents and the presence of water or degree of moisture may individually or collectively act to effect viability.

There are a number of techniques known in the art for stabilising proteins, some of which are briefly discussed below.

Freeze-drying under vacuum (lyophilisation) is commonly used to prepare proteins for use in vaccines and the like. Freeze-drying traditionally involves freezing a solution of the biological protein and removing ice crystals there from by converting them into water vapour under vacuum (sublimation). This process often results in damage to the native structure of the protein.

To help increase the stability of a biological protein being prepared by freeze-drying, additives such as buffering or stabilising agents may be used in the product formulation. However, during freeze-drying, when the temperature of the solution is slowly reduced to minus 20° C. over a period of days, the additives may solidify at different freezing points. As a result, the end product may be a fine puffy cake-like substance actually made up of different layers each representing an individual component. In essence, the additives added to protect the biological protein may be physically and chemically separated there from rendering them useless as protective agents.

An alternative procedure, which is commonly used in the food and dairy industries to make dry fruit concentrates and milk powders, for example, is spray-drying-using-heat. This process involves spraying a fine mist of solution downwards from the top of a spray tower against an upward current of hot air. The hot air removes water from the droplets before they reach the bottom of the tower. Spray drying normally operates at an inlet air temperature exceeding 190° C. and the product temperature may well exceed 60° C. In this operating environment most of the biological protein or cells, such as bacterial cells, denature.

Another protein preparation process known in the art is supercritical fluid drying. In this process, biological agents such as peptides, proteins and nucleic acids are maintained in an aqueous solution until particle formation. The aqueous solvent is removed at the time of particle formation using controlled hydrogen-bonding solvents, such as ethanol, and isopropanol.

Fluid bed spray drying is a modified spray-drying-using-heat technology. The process is commonly used in the pharmaceutical and chemical industry for tablet granulation and/or for drying heat stable materials. The process involves spraying a fine mist of solution containing actives downward from the top of a spray head towards a mass of dry excipients. Simultaneously, an upward current of hot air is passed through the mass of excipients to create a fluidized bed. The hot air removes water from the fluidized wet solids at the bottom of the fluid bed.

Fluid bed spray drying technology may be applicable to pharmaceutical proteins which are heat stable around 50° C. to 60° C. However, the native structure of the protein may be compromised and accordingly the protein may loose all, or at least some, of its biological activity.

Further problems may be associated with fluid bed spray drying as described above; for example, the spray nozzles, which are positioned near the top of the processing chamber, are required to have substantial clearance above the surface of the fluidized bed of excipient materials so that the such materials do not block the spraying nozzles; a substantial amount of the coating material, or liquid containing the active ingredient(s), may block the nozzles' filter system leading to processing loss; and such top spraying fluid bed operation may only be ideal for granulation rather than for spray coating purposes. The fluid bed spray drying process also typically provides coarse and irregular granules having different shapes and sizes. Contact between the granules results in a grinding effect which may result in denaturation of the protein.

Of the techniques in commercial use prior to the development of the present invention, for preparing biological proteins and cells, the technique of microencapsulation may be considered the most useful. Typically, no major equipment is required and the batch size can be as small as 10 g to 20 g thus making it useful for the preparation of biological proteins that may not be plentiful. This process uses organic solvents to solubilize the biological protein which is then encapsulated in polymeric microspheres using either a water-in-oil-in-water (w/o/w) or a solid-in-oil-in-water (s/o/w) emulsion method. Protein is captured into the solid microspheres after water is removed by simple filtration and the solvent is evaporated off.

Microencapsulation technology has been used to make carbon or self-adhesive paper in the paper industry and at least in Japan, food products, such as artificial fish eggs and decorative products are made using gelatine microcapsules to entrap fish or meat flavours.

While microencapsulation may be considered a favourable means to prepare biological proteins and whole cells for storage and future use, the technology is still at the developmental stage in the pharmaceutical and biotechnological industries. The technology has apparent difficulties in that proteins are likely to be denatured by the solvents used and by the necessary emulsifying/homogenising process. In addition, the quality of a product produced according to this process, may be considered undesirable due to the fact that traces of solvent remain in the core of the microcapsules which may hamper the commercialisation of a product produced using this technology.

The present inventor has developed an alternative process based on spray-drying-using heat and microencapsulation technology in which active components, such as proteins, may be stabilised for extended periods.

SUMMARY OF THE INVENTION

In a first aspect, the present invention provides a process for preparing a product comprising at least one active component, the process comprising:
(i) providing a coating liquid comprising at least one active component, a saccharide and a water-miscible solvent;
(ii) providing particles comprising one or more water-soluble gel-forming compounds;
(iii) fluidising the particles within a processing chamber of an apparatus in such a manner that the particles move in an upward direction within the chamber in a helical path;
(iv) spraying the coating liquid onto the particles so as to provide coated particles;
(v) allowing the coated particles to dry.

The at least one active component may be unstable.

The at least one active component may be unstable in the presence of light, heat, air and/or moisture.

The at least one active component may be a biological material, for example a protein, a peptide, live cells or a microorganism.

The at least one active component may be an unstable biological material.

The at least one active component may be a light, heat, air and/or moisture-sensitive biological material.

The at least one active component may be a cytokine.

The at least one active component may be selected from the group consisting of: an interleukin, an interferon, EPO, Exenatide G-CSF, human growth hormone and thymosine.

The at least one active component may be selected from the group consisting of: an anti-cancer agent, an anti-inflammatory agent, a hemolytic agent, an anti-diabetic agent, an anti-allergy agent and an anti-fungal agent.

The processing chamber may be at a temperature between about 30° C. and 45° C. or at a temperature between about 35° C. and 40° C. during performance of the process.

The coating liquid may be in the form of microdroplets prior to contacting the particles.

The coating liquid may be converted into a solid state on the particles within one second of entering the processing chamber.

Prior to step (iii), the particles may be fluidised in the processing chamber and dried by application of heat thereto.

The particles may be dried by heating to a temperature between about 30° C. and 80° C.

In step (iii), the particles may rotate.

Step (iii) may be performed by introducing an upward moving rotating gas flow into the processing chamber thereby causing the particles to move in an upward direction in a helical path.

Step (iii) may be performed by drawing gas through a guide member located at the bottom of, or adjacent to the bottom of, the processing chamber, where upon exiting the guide member the gas moves upwards in a rotating path thereby causing the particles to move in an upward direction in a helical path.

The guide member may comprise an inlet into which a gas is drawn and an outlet from which the gas is discharged, the guide member comprising a gas directing element which acts on the gas passing between the inlet and the outlet such that gas discharged from the outlet moves upward in a rotating path.

The guide member may comprise at least two members which are adapted to rotate about a common axis, wherein a first member includes an inlet into which a gas is able to be drawn and wherein a second member includes one or more gas directing elements which project outwardly from a surface of the second member, wherein the second member is located above the first member and wherein in use gas drawn into the inlet acts on the one or more gas directing elements causing the second member to rotate such that gas discharged from the guide member moves in an upwards direction in a rotating path.

The gas may be air or an inert gas, for example nitrogen.

The gas may be at a temperature between about 30° C. and 45° C., or between about 35° C. and 40° C. when entering the processing chamber.

Prior to commencement of step (iii) or step (iv), air in the processing chamber may be replaced with an inert gas, for example nitrogen.

Step (iv) may comprise spraying the coating liquid from the bottom of the processing chamber toward the particles.

Step (iv) may comprise spraying the coating liquid in an upwards direction such that the coating liquid moves along a column created by flow of the particles.

Step (iv) may comprise spraying the coating liquid in an upwards direction towards the particles at an angle of between about 10° and 70°, or at an angle between about 20° and 60°, or at an angle between about 30° and 50°, or at an angle between about 35° and 45°, or at an angle of about 40°.

Step (iv) may comprise spraying the coating liquid from multiple spray outlets within the processing chamber.

In step (iv) the coating liquid may be at a temperature between about 0° C. and 50° C., or at a temperature between about 10° C. and 50° C., or at a temperature between about 15° C. and 45° C., or at a temperature between about 30° C. and 45° C., or at a temperature between about 35° C. and 40° C. In one embodiment, the coating liquid may be at room temperature, for example about 20° C.

Step (v) may comprise allowing the coated particles to heat dry.

Steps (iv) and (v) may be performed under equilibrium conditions.

The process may further comprise one or more additional coating steps which further coat the particles with a coating selected from the group consisting of: an enteric coating, a film coating, a moisture-repellant coating and a taste-masking coating.

The coating liquid may further comprise additional components selected from the group consisting of: amino acids such as lysine, arginine, cysteine and leucine, proteins such as human serum albumin, egg albumin, chelating agents such as EDTA and sodium EDTA, buffers such as sodium phosphate buffers, citric acid/citrate buffers, tris buffer, preservatives such as hydroxybenzoic acid and derivatives thereof, stabilisers, antioxidants such as vitamin E, ascorbic acids, and lubricants such as water, silicone and silicates.

The water-miscible solvent may be a glycol, for example glycerol or propylene glycol.

The saccharide may be a sugar polymer.

The saccharide may be selected from the group consisting of: fructose, glucose, invert sugar, lactitol, lactose, maltitol, maltose, mannitol, sorbitol, sucrose, trehalose, mannitol and combinations thereof.

The one or more water-soluble gel-forming compounds may be selected from the group consisting of: acrylate and derivatives thereof, albumin, alginates, carbomers, carrageenan, cellulose and derivatives thereof, dextran, dextrose, dextrin, gelatin, polyvinylpyrrolidone, starch, pregel starch and combinations thereof.

The process may be performed in an inverted fluidised bed reactor.

The processing chamber of the apparatus may be enclosed.

The processing chamber of the apparatus may be a sterile environment.

The processing chamber of the apparatus may be an inert environment.

The particles may be microparticles.

In a second aspect, the present invention provides a product comprising at least one active component whenever prepared by the process of the first aspect.

The at least one active component may be selected from the group consisting of: an interleukin, an interferon, EPO, Exenatide, G-CSF, human growth hormone and thymosine.

The at least one active component may be selected from the group consisting of: an anti-cancer agent, an anti-inflammatory agent, a hemolytic agent, an anti-diabetic agent, an anti-allergy agent and an anti-fungal agent.

In a third aspect, the present invention provides use of a product of the second aspect for delivering at least one active component to a subject.

The subject may be a human or animal.

The product may be adapted for injection, oral or nasal administration, sublingual administration, topical administration or vaginal or rectal administration.

The product may be in a dosage form selected from the group consisting of: a composition intended for injection, a sublingual tablet, an oral tablet, a sustained release sublingual tablet, microcapsules intended for filling into capsules, microcapsules, a feed premix, a pessary, a pre-constituted solid dose intended for nasal spray or drops, aqueous drops, an eye wash or drops and a skin washing solution.

The product may be in a dosage form selected from the group consisting of: a sustained release tablet or microcapsules.

In a fourth aspect the present invention provides use of the process of the first aspect for stabilising at least one active component.

In a fifth aspect, the present invention provides use of the process of the first aspect for preparing sustained release dosage forms.

For the purpose of the second, third, fourth and fifth aspects, the at least one active component may be an active component as defined in the first aspect and as described herein.

In a sixth aspect, the present invention provides an apparatus for preparing a product comprising at least one active component comprising: a processing chamber in which is located one or more outlets for introducing a liquid into the processing chamber, an inlet located at the bottom of the processing chamber and an outlet, thereby permitting the movement of gas through the processing chamber, wherein the inlet is provided with a guide member such that when gas is drawn through the inlet, upon exiting the guide member the gas moves in an upward direction in a rotating path.

The guide member may be a guide member as described herein.

BRIEF DESCRIPTION OF THE FIGURES

A preferred embodiment of the present invention will now be described, by way of example only, with reference to the accompanying figures wherein.

DEFINITIONS

The following are some definitions that may be helpful in understanding the description of the present invention. These are intended as general definitions and should in no way limit the scope of the present invention to those terms alone, but are put forth for a better understanding of the following description.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

In the context of this specification, the term "about" is understood to refer to a range of numbers that a person of skill in the art would consider equivalent to the recited value in the context of achieving the same function or result.

In the context of this specification, the terms "a" and "an" are used herein to refer to one or to more than one (i.e. to at least one) of the grammatical object of the article. By way of example, "an element" means one element or more than one element.

In the context of this specification, the term "microparticles" is understood to include particles having a diameter between about 50 and 800 microns, and preferably between about 200 and 400 microns.

In the context of this specification, the term "equilibrium conditions" is understood to mean that the amount of moisture input is equal to the amount of moisture lost from the particles by evaporation as a result of input heat.

In the context of this specification, the term "active component" is to be construed in its broadest sense and includes, for example, drugs, live cells including parts thereof, proteins, peptides, nucleic acids, viruses, virus particles, microorganisms and the like, or any other matter or material which may be administered to a subject, such as a human or animal for any purpose, including therapeutic purposes.

In the context of this specification, the term "unstable" is understood to mean that the material to which it refers is susceptible to unwanted change, be it physical or chemical, under particular conditions, for example atmospheric conditions.

DETAILED DESCRIPTION OF THE INVENTION

The present invention broadly relates to a process for preparing products comprising an active component. The products obtained by the process may be referred to as "microcapsules". In certain embodiments the invention provides a process for stabilising/preserving unstable materials, for example light, heat, air and/or moisture-sensitive materials, and in particular biological materials such as for example, proteins, peptides, live cells and microorganisms. The process of the invention finds particular application in the stabilisation/preservation of proteins and peptides which are intended for administration to humans or animals. The stabilised products produced by the process of the invention result in improved efficacy of constituent proteins or peptides when administered to subjects. The process of the invention may be performed at an operating temperature of only 30° C. to 40° C. meaning that it is compatible with many active components that are heat sensitive.

In one aspect, the invention provides a process for preparing a product comprising at least one active component, the process comprising:
  (i) providing a coating liquid comprising at least one active component, a saccharide and a water-miscible solvent;
  (ii) providing particles comprising one or more water-soluble gel-forming compounds;
  (iii) fluidising the particles within a processing chamber of an apparatus in such a manner that the particles move in an upward direction within the chamber in a helical path;
  (iv) spraying the coating liquid onto the particles so as to provide coated particles;
  (v) allowing the coated particles to dry.

In general terms, the process involves the spraying of a liquid comprising an active component in combination with at least one saccharide and a water-miscible solvent onto an acceptable particulate excipient material (particles, preferably microparticles) in an appropriate processing chamber, wherein when coated, the particles are moving upwards through the chamber in a helical path/trajectory. The movement of the particles in the processing chamber resembles that of air movement in a hurricane. The coating of the particles results in micro-encapsulation and hence stabilisation/preservation of the active component. The helical trajectory of the particles in the processing chamber provides for a smooth, even coating of the coating liquid which forms a hydrogel comprising the active component and other water-soluble materials, such as sugars and amino acids.

The nature of the coating liquid and particles are such that the products produced by the process find particular application in sustained release delivery applications, such as mucosal and sublingual delivery of therapeutically active components. In such applications the water-soluble materials dissolve when contacted with saliva resulting in the generation of micropores on the coating surface which facilitate disintegration of the microcapsules into a liquid gel. The gel lines the mucosal surface thereby delivering the active component and optimising absorption. Accordingly, products prepared in accordance with the process of the present invention represent convenient solid oral delivery forms for therapeutically active components that may replace the need for injections.

The process of the invention also allows successful preparation of dosage forms having parts per billion of an active component which is distributed evenly therein. The in vivo action of cytokines is often catalytic and hence in order to achieve desired biological activities only nanogram or picogram quantities are required. Distributing such small quantities evenly in a solid mass is particularly difficult and without precedent in the pharmaceutical industry.

By utilising the process of the present invention active components may be encapsulated in a protected environment to the exclusion of water, light, oxygen and microbes. In the case of biological materials such as proteins and peptides, stability can be achieved over a period of up to four years without refrigeration.

The at least one active component may be unstable. In one embodiment the at least one active component is light, heat, air and/or moisture-sensitive. The at least one active component may be any biological material, including but not limited to: proteins, peptides, live cells, microorganisms and nucleic acids. The biological material may be unstable, for example light, heat, air and/or moisture-sensitive. In one embodiment the at least one active component is a cytokine such as an interleukin or interferon. In an alternative embodiment the at least one active component is an anti-cancer agent, an anti-inflammatory agent, a hemolytic agent, an anti-allergy agent, an anti-diabetic agent or an anti-fungal agent. The at least one active component may be a peptide, for example Exenatide. Those skilled in the art will recognise that the process of the invention is also applicable to a wide range of other active components in addition to those mentioned above, for example any material that requires stabilisation/protection for any reason whatsoever. In particular, the process of the invention is applicable to any unstable therapeutic materials intended for administration to humans or animals.

The coating liquid comprises at least one active component, a saccharide and a water-miscible solvent. The saccharide may be, for example, mannitol, trehalose, isomalt, xylitol, dextrose, dextran, fructose, glucose, invert sugar, lactitol, lactose, maltitol, maltose, maltodextrin, sorbitol, sucrose, or any combination thereof. However, it will be appreciated by those skilled in the art that alternative saccharides may be used depending for example on the nature of the active component contained within the solution and the intended use of the product. It is to be understood that the term "saccharide" used herein includes sugar alcohols such that the term "a saccharide" is synonymous with "a saccharide or sugar alcohol".

In some embodiments of the invention multiple coatings may be applied which comprise different constituents. For example, when preparing microcapsules comprising interferon, the first coating liquid applied may comprise gelatine or ovalbumin in propylene glycol and water. The second (or active) coating may comprise interferon, glycine, leucine, dextran, phosphate buffer, albumin, glucose, trehalose and maltodextrin.

Water-miscible solvents suitable for use in the process of the invention include any and all water-miscible solvents that are considered save for contact with tissues of the human or animal body based on a reasonable risk/benefit ratio. Preferably, the water-miscible solvent is a glycol such as glycerol or propylene glycol, or a mixture thereof. Other suitable water-miscible solvents will be apparent to those skilled in the art having regard to the intended use of the product.

The coating liquid may comprise additional components, including but not limited to: further proteins, amino acids, diluents, chelating agents, buffers, preservatives, stabilisers, antioxidants, lubricants and other additives which may act to compliment the function of, or stabilise, the particular active contained therein. Those skilled in the art will recognise that the nature of additional components present will depend primarily on the active component and the intended use of the product. Further examples of specific additional components include, but are not limited to: lysine, glycine, leucine, isoleucine, arginine and cysteine; human serum proteins, albumin, egg albumin and gelatin; sodium phosphate buffers, citric acid/citrate buffers, tris buffer; derivatives of hydroxybenzoic acids; vitamin E, ascorbic acid; water-miscible silicone/silicates; citric acid, EDTA and EGTA.

Those of skill in the art will appreciate that a variety of alternative proteins, amino acids, diluents, chelating agents, buffers, preservatives, stabilisers, antioxidants and lubricants may also be suitable for use in the present invention depending again on the nature of the active component and the intended use of the product.

The particles comprise water-soluble gel-forming compounds which may be either natural or synthetic polymers or monomers which preferably do not become liquids or semi-solids in the presence of relatively high moisture content. Suitable water-soluble gel-forming compounds include, but are not limited to: acrylate or derivatives thereof, albumin, alginates, carbomers, carrageenan, cellulose or derivatives thereof, dextran, dextrin, gelatine, polyvinylpyrrolidone, starch or combinations thereof. In one embodiment the water-soluble gel-forming compound is gelatine, pregel starch, carboxymethylcellulose, or a combination thereof. The water-soluble gel-forming compound may form part of the core of the particles. Such a core may be referred to herein as a "hydrogel" core. The particles may further comprise one or more simple sugars which may serve to influence the rate of dissolution of the product when subjected to an aqueous environment. The rate of dissolution of the product may be increased by increasing the percentage of simple sugar present in the core of the particles, or decreased by decreasing the percentage of simple sugar present in the core of the particles. In addition, by inclusion of one or multiple water-soluble gel-forming compounds in the core, and/or by increasing the molecular weight of the water-soluble gel-forming compounds, optimised sustained release solid dosage forms may be created.

The particles used in the process of the invention are preferably microparticles having a diameter between about 50 and 800 microns, or between about 100 and 600 microns, or between about 200 and 400 microns, however it will be appreciated that particles having alternative sizes may also be utilised depending on the active component and the intended use of the product. Small particles dissolve faster than larger ones as water is able to penetrate through the surface faster and into the core leading to gel formation. As such, use of a mixture of different size particles may optimise a continuous sustained release effect.

The composition of the particles used in the process ensures that the coating liquid comprising the active component binds efficiently to the surface of the particles without significant agglomeration or loss.

The process of the invention involves fluidising the particles within the processing chamber of an apparatus in such a manner that the particles move in an upward direction within the chamber in a helical path. The particles may also simultaneously rotate. The helical trajectory of the particles in the processing chamber results in a smooth, even coating of the coating liquid on the particles. A smooth, even coating is advantageous because it minimises abrasive interactions that may occur between rough, unevenly coated particles. Such abrasive action may have a detrimental effect on the active component, particularly in cases where the active component is a protein or peptide.

Helical movement of the particles may be achieved by causing gas (which may include air or an inert gas) in the processing chamber to move in a helical path. This may be achieved by introducing an upward moving rotating gas flow into the processing chamber. The upward moving rotating gas flow lifts particles from the bottom of the processing chamber causing them to move in an upward direction in a helical path. In one embodiment, helical movement of the particles is achieved by drawing gas through a guide member located at the bottom of, or adjacent to the bottom of, the processing chamber. Gas may be drawn through the guide member by placing the processing chamber under negative pressure conditions. The guide member is adapted to cause gas drawn there through to move upward in a rotating path, which in turn lifts the particles causing them to move in an upward direction in a helical path.

In one embodiment the guide member comprises an inlet into which a gas is drawn and an outlet from which the gas is discharged, the guide member comprising a gas directing element which acts on the gas passing between the inlet and the outlet such that gas discharged from the outlet moves upward in a rotating path.

In an alternative embodiment the guide member comprises at least two members which are adapted to rotate about a common axis, wherein a first member includes an inlet into which a gas is able to be drawn and wherein a second member includes one or more gas directing elements which project outwardly from a surface of the second member, wherein the second member is located above the first member and wherein in use gas drawn into the inlet acts on the one or more gas directing elements causing the second member to rotate such that gas discharged from the guide member moves in an upwards direction in a rotating path. In this embodiment, the first member may be in the form of a disk, and the second member may be in the form of a disk or a cone shape. In use, the second member may lift, become spaced apart from the first member and rotate such that gas discharged from the guide member moves in an upwards direction in a rotating path. The inlet may be located in the centre of the first member. The one or more gas directing elements may be located on a lower surface of the second member which faces the first member. The gas directing elements may be a plurality of curved blades. The diameter of the first member may be larger than the diameter of the second member. The guide member may further comprise a third member located between the first and second members, the third member comprising an inlet in communication with the inlet of the first member and further comprising one or more gas directing elements which project outwardly from a surface of the third member, wherein in use gas drawn into each inlet acts on the one or more gas directing elements causing the second and third members to rotate such that gas discharged from the guide member moves in an upwards direction in a rotating path. In use, the second and third members may lift so that the first, second and third members are spaced apart and rotate such that gas discharged from the guide member moves in an upwards direction in a rotating path. The gas directing elements of the third member may be a plurality of curved blades. The third member may be in the form of a disk. The diameter of the third member may be larger than the diameter of the second member and smaller than the diameter of the first member. The one or more gas directing elements may be located on a lower surface of the third member which faces the first member.

In an alternative embodiment, the guide member comprises at least four members, which are provided in the form of a first disk, second disk, third disk and a cone in a stacked configuration being rotatable about a common axis, wherein each of the first, second and third disks include an inlet central thereto into which a gas is able to be drawn, and wherein a surface of each of the second disk, third disk and cone include a plurality of gas directing elements which project outwardly from a surface thereof, wherein in use gas drawn into each inlet acts on the one or more gas directing elements causing the second disk, third disk and cone to rotate such that gas discharged from the guide member moves in an upwards direction in a rotating path. In this embodiment, the first disk may have a larger diameter than the second disk, the second disk may have a larger diameter than the third disk, and the third disk may have a larger diameter than an end face of the cone, such that when the disks and cone are stacked together the guide member has an overall conical appearance with a base provided by the first disk and a tip provided by the cone. The one or more gas directing elements may be located on a lower surface of the second and third disks and on a surface of the cone that faces the third disk. The gas directing elements may be a plurality of curved blades. In use, the second disk, third disk and cone may lift so that the first disk, second disk, third disc and cone become separated and rotate such that gas discharged from the guide member moves in an upwards direction in a rotating path.

In a further embodiment of the invention the guide member comprises three circular members having central holes defining a path there through. The circular members are adapted to rotate about a common axis, and are of decreasing diameter commencing from the member located at the lowest point of the processing chamber. The ratio of the diameters of the circular members is approximately 2:1.5:1. Atop the circular members is a solid cone-shaped member which is adapted to rotate about the same axis as the circular members. The cone-shaped member has a diameter that is smaller than the diameter of the circular member directly below it. The edges of the two circular members located directly below the cone-shaped member are sloped such that when the two circular members and the cone-shaped member are placed together the three sections form a larger cone shape having a continuous flat surface. With the exception of the circular member located at the lowest point of the processing chamber, the lower sides of the circular members comprise a plurality of generally curved blades extending from the outer edge toward the central holes. The blades function to direct air flow toward the holes. In use, negative pressure is applied to the processing chamber resulting in gas being drawn upwards through the circular sections. In the presence of continuous gas flow the circular sections and the cone-shaped section lift, become spaced apart from one another and rotate. The combined effect of the spinning sections and the curved blades causes gas exiting the guide member to move upwards in a rotating path, or in other words a path that resembles air movement in a hurricane. The upward moving rotating gas flow lifts particles from the bottom of the processing chamber causing them to move in an upward direction in a helical path.

The guide member described in the preceding paragraph may be referred to herein as "Rocket Drive".

The step of spraying the coating liquid typically occurs from the bottom of the processing chamber in an upwards direction. Accordingly, the coating liquid is sprayed in the same general direction of movement as that of the particles through the processing chamber. In one embodiment, the coating liquid is sprayed in an upwards direction such that the coating liquid moves along a column created by flow of the particles within the processing chamber. The movement of the particles in a helical path within the processing chamber creates a column shape having an outer surface. In this embodiment the coating liquid is sprayed in an upwards direction so that the liquid moves along the outer surface of the column of particles. In an alternative embodiment, the coating liquid may be sprayed in an upwards direction towards the particles at an angle between about 20° and 60°, or at an angle between about 30° and 50°, or at an angle between about 35° and 45° (with respect to the bottom of the processing chamber). The precise angle at which the coating liquid is sprayed will depend on the dimensions of the processing chamber. For example, where a tall, narrow processing chamber is employed the angle required is likely to be in the order of 40° to 50°. Alternatively, where a wider, shorter processing chamber is employed the angle required is likely to be less than 40°. Those skilled in the art will be capable of determining the most appropriate angle at which the coating liquid is sprayed by routine trial and experimentation having regard to the dimensions of the processing chamber.

The coating liquid may be at a temperature between about 0° C. and 50° C., or at a temperature between about 10° C. and 50° C., or at a temperature between about 15° C. and 45° C., or at a temperature between about 30° C. and 45° C., or at a temperature between about 35° C. and 40° C. Alternatively, the coating liquid may be at room temperature when entering the processing chamber.

Depending on the intended batch size, the processing chamber may comprise one or a plurality of spray guns from which the coating liquid is ejected. When using multiple spray guns, different guns can be charged with different coatings. The spray guns may be activated at any time during performance of the process, in combination, in series or in sequence. This provides significant flexibility for producing products having multiple coating layers and different active components. In contrast to a freeze dried powder in a vial, the process of the present invention makes it possible to produce a product with many active components in a single solid dose. By encapsulating one active component at a time and then mixing the microcapsules obtained, the process of the invention makes it possible to combine chemically and/or physically incompatible components into a single dose.

The spray guns employed in the process of the invention may be adapted such that the coating liquid is converted into microdroplets prior to contacting the particles. The size of the microdroplets may be altered by controlling the spray rate and the volume of gas entering the processing chamber.

Following spraying, the coating liquid is transformed into a continuous glassy film (a "bioglass") that is wrapped around the particles. The transformation from liquid to glassy solid is rapid (less than 1 second) so as not to compromise the stability of the active component. The active component will not be damaged by heat as this is dissipated by the latent heat of evaporation of water.

Additional coating steps may be performed as desired in order to obtain products having particular characteristics. For example, prior to or after the drying step, the resultant product may be coated with further coatings. Those skilled in the art will recognise situations where this may be advantageous, for example where a product is desired to be administered orally, enteric coatings may be utilized so as to protect the product from degradation in the stomach. Generally, such further coating will be carried out at a similar coating rate to that used for coating the particles with the initial coating liquid.

The process of the invention is preferably conducted in an enclosed sterile environment, or in other words an environment that is free, or substantially free of contaminants. Generally contaminants comprise microorganisms and the like, however those skilled in the art will readily appreciate that it is desirable to also exclude any other deleterious contaminants when performing the process of the invention.

The environment in which the process is conducted is preferably free, or substantially free of oxygen so as to minimise the possibility of oxidation of active components. An oxygen-free or substantially oxygen-free environment may be achieved by replacing the air contained within the processing chamber, with an inert gas, for example nitrogen. It will however be appreciated that alternative inert gases may be utilised, for example carbon dioxide or argon.

The process of the present invention may involve the over weighting of the particles in the processing chamber. In normal fluid bed operation it is recommended by equipment manufacturers not to exceed 50% w/v capacity of the processing chamber. For example, if the processing chamber is 100 L, processing material weight should not be more than 50 kg. However, the process of the present invention allows for the processing weight to chamber volume to be more than 100% w/v. Accordingly, the processing weight of particles in any one batch can be at least doubled or even tripled resulting in a significant improvement in production efficiency, and significant capital savings when compared to a normal fluid bed spray coating system.

In order to minimise damage to the active component the process may be carried out under equilibrium conditions. In this regard, the amount of moisture input is equal to the amount of moisture lost from the particles by evaporation as a result of input heat. Accordingly, the process may be conducted in a moisture and heat neutral environment. In a "moisture and heat neutral environment" the conditions are such that the surface of the microparticles is moisture free. A moisture free environment may be achieved by setting the spray rate equal to the evaporation rate at a constant temperature.

The process of the invention may be carried out in any appropriate fluid bed spraying apparatus. In the Examples that follow a "Rocket Drive" designed by Vitapharm Technology Development Co. Ltd in BDA, Beijing, China manufactured by Hinge Engineering located within a CPU Driven Turbojet™ Fluid Bed Coater manufactured by BWI Huttlin (Daimlerstrasse 7, D-79585, Steinen, Germany) is used. Persons skilled in the art will be familiar with the BWI Huttlin apparatus.

It will be appreciated that modifications may be made to the apparatus in order to facilitate efficient and effective microencapsulation. For example, the apparatus used in the Examples described herein may be custom modified as follows:

The spray nozzle was redesigned such that the centre part of the nozzle (which delivers the coating liquid to the processing chamber) may be removed during operation of the apparatus for cleaning or unblocking. This modification allows for continuous operation of the apparatus.

All contact surfaces were exhaustively mirror polished so as to facilitate heat sterilisation after the standard Cleaning-In-Place cycle.

Replacement of air introduced into the processing chamber with a recirculating inert gas, such as nitrogen, which may be used for fluidisation as opposed to air. This modification may minimise oxidation of susceptible active components and increase the stability of anaerobic bacteria.

The central air return column present in the standard apparatus is replaced with the Rocket Drive guide member described above.

In one embodiment, the process of the invention (for a 2 to 3 Kg batch) may be carried out as follows:

1. Solid hydrogel particles (microparticles) having a suitable composition are loaded into the Rocket Drive-equipped Huttlin Turbojet™ Fluid Bed Coater by vacuum and are fluidised. Fluidisation occurs at a rate of between 500 and 1000 $m^3$/hr of air.
2. The microparticles are heated to a temperature between about 30° C. and 80° C., more preferably to a temperature of about 60° C., for approximately one hour with low velocity processing air (which enters the processing chamber via the Rocket Drive) such that they are fluidised in a slow motion. Slow motion fluidisation ensures that the inner portion of the microparticles is dry and minimises interparticle friction.
3. The temperature of the microparticles is then reduced to about 35° C. to 45° C. and the processing air velocity entering the processing chamber is increased until the microparticles move upwards in a helical trajectory.
4. When the temperature of the microparticles reaches about 35° C. to 45° C. the processing air is replaced by an inert gas, such as nitrogen. This step may be performed for at least about 5 minutes to ensure that all air present in the processing chamber is replaced with the inert gas.
5. The active component is immobilised in an appropriate coating liquid. The base solution is heated to about 38° C. in order to allow complete solid dissolution. Just prior to spray coating the active component is added to the base solution (mixing at approximately 60 rpm) and mixed well.
6. A desired quantity of coating liquid is then sprayed onto the fluidised microparticles, preferably at the highest speed possible, whilst the microparticles are moving upwards in a helical trajectory. Coating takes place at a rate of about 20 grams to 40 grams of coating liquid per minute. The coating liquid is sprayed from the bottom of the processing chamber at an angle of about 40° to 50° (with respect to the bottom of the processing chamber) towards the moving microparticles.
7. The coating speed is preferably between about 25 grams to 35 grams of coating liquid per minute when the microparticles are free from excess moisture thereby ensuring that the microparticles move continuously in a helical manner. Accordingly, the coating liquid (containing an active component such as a protein or peptide) is continuously dehydrated in a moisture-free nitrogen environment. The product is typically dried to a water activity of less than 0.25.

It will be appreciated that the above processing steps and parameters may be altered to accommodate the production of various products or products comprising different actives. Alterations may be made for example to: the inlet process air temperature, the product temperature, the fluidised air volume, the liquid spraying speed, the coating liquid temperature, the coating liquid viscosity, the coating liquid solid content, the total core surface area of the microparticles, the water solubility of the core of the microparticles, the humidity of the inlet air, the compressed air spraying pressure, the apparatus filter pore size and the frequency of auto dedusting. Where an alteration is made to one parameter, persons skilled in the art will readily be able to identify any corresponding adjustments that may be required to another parameter in order to compensate for the initial alteration.

In the process of the invention the batch size may vary according to the volume of the processing chamber and whether overloading is required. In the Examples described herein the batch size is typically 3 kg. In this context, "Batch size" refers to the total solids used in the process and includes solids contained in both the microparticles, coating liquid, and any additional coating liquids employed. Accordingly, as used herein percentages of particular components are expressed in terms of the percentage of the total batch size.

The present invention further relates to products comprising at least one active component that are prepared by the process of the invention. Preferably, the products comprise biological materials, however those skilled in the art will appreciate that the products may comprise any material that is potentially light, heat, moisture or air sensitive, or that requires stabilisation/protection for any reason whatsoever. The present invention further relates to use of the process of the invention for stabilising at least one active component.

The present invention further relates to the use of a product of the second aspect for delivering at least one active component to a human or animal. The products produced in accordance with the process of the invention find particular application in the delivery of active components, preferably biologically active components, to humans and animals. The product may be adapted for injection, oral or nasal administration, sublingual administration, topical administration, vaginal administration or rectal administration. The product may be in a dosage form selected from the group consisting of: a composition intended for injection, a sublingual tablet, an oral tablet, a sustained release sublingual tablet, microcapsules intended for filling into capsules, microcapsules, a feed premix, a pessary, a pre-constituted solid dose intended for nasal spray or drops, aqueous drops, an eye wash or drops and a skin washing solution. By virtue of the use of a water-soluble gel-forming compound the products produced in accordance with the invention are highly effective for sustained release delivery of active components via the sublingual and mucosal routes. Accordingly, a further aspect of the present invention involves the use of the process of the invention for preparing sustained release dosage forms. In one embodiment, delivery formulations in accordance with the invention comprise proteins and peptides, preferably proteins and peptides intended for therapeutic application, for example cytokines such as interleukin and interferon.

The present invention also relates to an apparatus for preparing a product comprising at least one active component comprising: a processing chamber in which is located one or more outlets for introducing a liquid into the processing chamber, an inlet located at the bottom of the processing chamber and an outlet, thereby permitting the movement of gas through the processing chamber, wherein the inlet is provided with a guide member such that when gas is drawn through the inlet, upon exiting the guide member the gas moves in an upward direction in a rotating path. The apparatus may be used to perform the process of the invention. The guide member used in the apparatus of the invention may be a guide member as described herein above in connection with the first aspect. The outlet may be located at the top of the processing chamber.

EXAMPLES

Example 1

Slow Release Interleukin 2 Tablet Containing 350 ng of Human Recombinant Interleukin 2 (IL2) per 200 mg Tablet Batch size: 3 kg
Container size: 1.5 L
Coating temperature: 38° C.±2° C.
Spray rate: 30 gram/minute
Typical microparticle core size: 700 μm-425 μm 30%), 425 μm-180 μm (55%), <180 μm (15%)
Hydrogel microparticle core: mannitol (70%), CMC sodium (2%), polyvinylpyrrolidone (2%), gelatin (13%) and starch (13%).
Coating liquid: mannitol (10%), propylene glycol (3.5%), succinylated gelatin (0.6%), glycine (0.3%), ascorbic acid (0.3%), albumin (0.05%), standard sodium phosphate buffer to pH 7 and water for injection to 100%.
The method was performed as follows:

1. Glycine, mannitol, succinylated gelatin, propylene glycol, ascorbic acid and the buffer are dissolved in water for injection and then filtered through a 0.2 micron membrane filter. Albumin is added followed by water for injection to make up the weight.
2. The processing chamber of the Rocket Drive-equipped Huttlin Turbojet™ Fluid Bed Coater is sterilised by heat treatment as instructed by the manufacturer for one hour.
3. The apparatus is then switched to circulating filtered nitrogen mode.
4. The microparticles are loaded into the processing chamber by vacuum, fluidised and then heated to a temperature of about 60° C. for one hour.
5. The temperature of the microparticles is then reduced to 40° C.
6. The contents of the processing chamber are then fluidised at a rate of 300 $m^3$/hr of air, which is slowly increased to 900 $m^3$/hr of air as required. This results in the microparticles moving in an upward direction in a helical path.
7. Sterile IL2 (recombinant human IL2 (2.25 mg)), is then added to the coating liquid which is then sprayed upwards from the bottom of the processing chamber under equilibrium conditions towards the microparticles at a rate of 30 g/minute.
8. The resultant product is dried to less than 0.25% water activity content.
9. The product is then compressed, according to standard procedures in the art, into 200 mg tablets.
10. The tablets are then packaged in nitrogen flushed aluminium/aluminium foil packs and stored at a temperature not exceeding 25° C.

Process Validation Results

Two batches of IL2 350 ng tablets were processed on the same day using the same equipment, operational parameters and the same batch of active and excipient materials. Batches produced in the morning and afternoon were assigned a batch code of BX20100831-1 and BX20100831-2 respectively. Tablets were also made using the two batches of IL2 microcapsules. Each tablet has a mass 200 mg. Tablet specification=350 ng IL2±30%

| Batch # | Batch Yield | MicroCap Quantitative Eliza Assay 200 mg contains | Tablet Quantitative Eliza Aassay 200 mg contains | MacroCap Qualitative Bio Assay (CTLL-2 cell/ MTT) 200 mg cotains | Tablet Qualitative Bio Assay (CTLL-2 cell/MTT) 200 mg contains | Microcap activity to spec (350 ng ± 30%/ Tab) | Tablet Activity to spec (350 ng ± 30%/ Tab) |
|---|---|---|---|---|---|---|---|
| BX20100831-1 | 100% | 400 ng IL2 | 409 ng IL2 | 350 ng IL2 | 348 ng IL2 | 100% | 99% |
| BX20100831-2 | 100% | 412.5 ng IL2 | 375 ng IL2 | 351 ng IL2 | 319 ng IL2 | 100% | 91% |

ELISA and Bio Assay Validation Results

Two batches of IL2 250 ng tablets were processed on two separate days using the same equipment, operational parameters and the same batch of active and excipient materials. Batches produced on day 1 and day 2 were assigned batch codes of BX20100414-1 and BX20100422-1 respectively. Tablets were also made using the two batches of IL2 microcapsules. Each tablet has a mass of 200 mg. Tablet specification=250 ng IL2±30%.

| Batch # | Zero time | 6 months at 25 C. | % loss |
|---|---|---|---|
| BX20100414-1 | 246 ng IL2 | 221 ng IL2 | 10% |
| BX20100422-1 | 257 ng IL2 | 244 ng IL2 | 5% |

Example 2

Slow Release Exenatide Tablet Containing 20 Micrograms of Exenatide Per 200 mg Tablet Batch size: 3 kg
Container size: 1.5 L
Coating temperature: 38° C.±2° C.
Spray rate: 30 gram/minute
Typical microparticle core size: 700 μm-425 μm (30%), 425 μm-180 μm (55%), <180 μm (15%)
Hydrogel microparticle core: mannitol (66%), CMC sodium (4%), polyvinylpyrrolidone (2%), gelatin (13%) and starch (15%)
Coating liquid: mannitol (10%), propyleneglycol (3.5%), succinylated gelatin (0.6%), glycine (0.3%), dextran (0.3%), albumin (0.05%), standard sodium phosphate buffer to pH 7 and water for injection to 100%.
The method was performed as follows:
1. Glycine, mannitol, succinylated gelatin, propylene glycol, dextran and the buffer are dissolved in water for injection and then filtered through 0.2 micron membrane filter. Albumin is added followed by water for injection to make up the weight.
2. The processing chamber of the Rocket Drive-equipped Huttlin Turbojet™ Fluid Bed Coater is sterilised by heat treatment as instructed by the manufacturer for one hour.
3. The apparatus is then switched to circulating filtered nitrogen mode.
4. The microparticles are loaded into the processing chamber by vacuum, fluidised and then heated to a temperature of about 60° C. for one hour.
5. The temperature of the microparticles is then reduced to 40° C.
6. The contents of the processing chamber are then fluidised at a rate of 300 m³/hr of air, which is slowly increased to 900 m³/hr of air as required. This results in the microparticles moving in an upward direction in a helical path.
7. Sterile Exenatide (300 mg) is then added to the coating liquid which is then sprayed upwards from the bottom of the processing chamber under equilibrium conditions towards the microparticles at a rate of 30 g/minute.
8. The resultant product is dried to less than 0.25% water activity content.
9. The product is then compressed, according to standard procedures in the art, into 200 mg tablets.
10. The tablets are then packaged in nitrogen flushed aluminium/aluminium foil packs and stored at a temperature not exceeding 25° C.

Human Data

Figure 1:
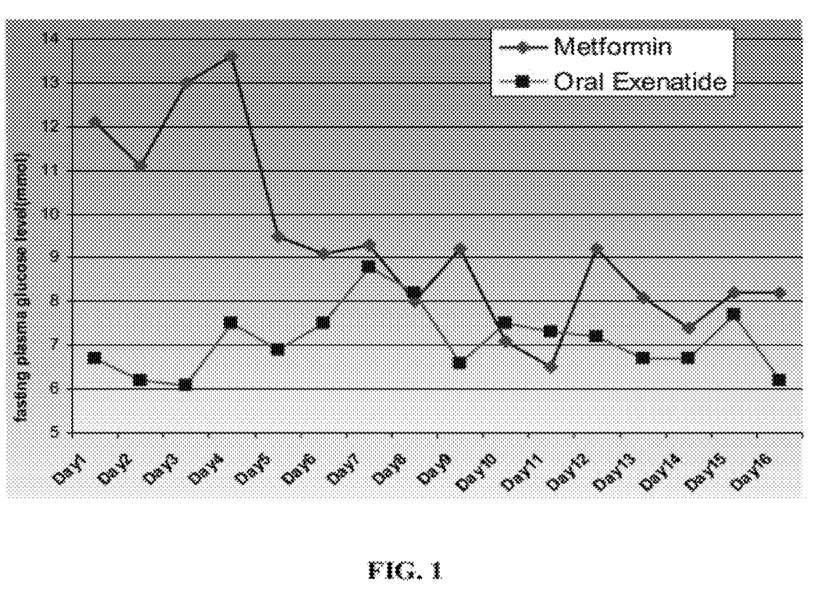
FIG. 1 shows the fasting plasma glucose levels of a human subject treated with metformin and an oral (sublingual) Exenatide product prepared in accordance with the process of the present invention.
Figure 2:
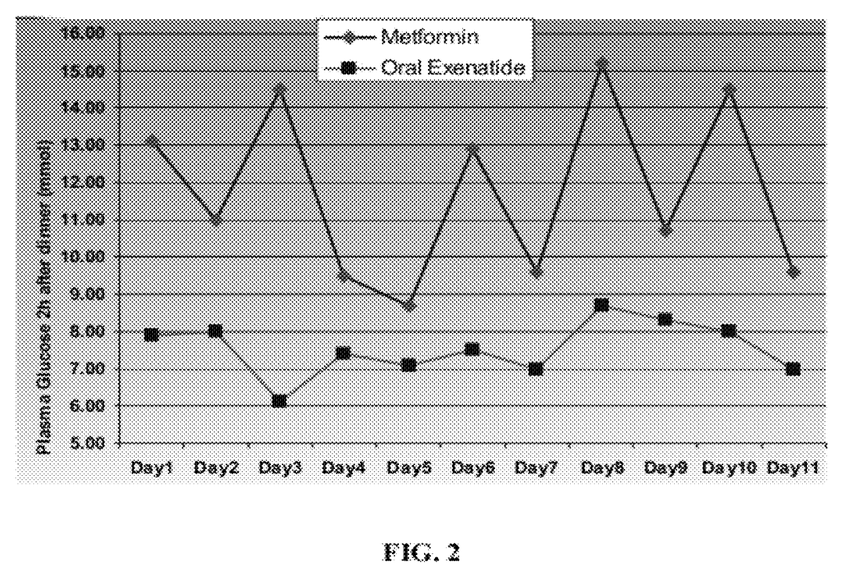
FIG. 2 shows the plasma glucose levels of a human subject treated with metformin and an oral (sublingual) Exenatide product prepared in accordance with the process of the present invention 2 hours after a meal.

A diabetic patient who was undergoing treatment with Metformin switched to once a day treatment with a slow release 20 μg Exenatide sublingual tablet prepared in accordance with Example 2. The fasting glucose and plasma glucose levels were measured and are depicted in FIGS. 1 and 2. When the patient took Metformin his blood glucose level was erratic and difficult to control. The patient then commenced treatment with the sublingual Exenatide tablets (under medical supervision) which provided a very steady blood glucose profile.

Those skilled in the art will appreciate that the invention described herein is susceptible to variations and modifications other than those specifically described. It is to be understood that the invention includes all such variations and modifications.

The claims defining the invention are as follows:

1. A process for preparing a product comprising at least one active component, the process comprising:
    (i) providing a coating liquid comprising the at least one active component, a saccharide and a water-miscible solvent;
    (ii) providing particles comprising one or more water-soluble gel-forming compounds;
    (iii) fluidising the particles within a processing chamber of an apparatus in such a manner that the particles move in an upward direction within the chamber in a helical path;
    (iv) spraying the coating liquid onto the particles so as to provide coated particles;
    (v) allowing the coated particles to dry.
2. The process of claim 1, wherein the at least one active component is unstable.
3. The process of claim 2, wherein the at least one active component is unstable in the presence of light, heat, air and/or moisture.
4. The process of claim 1, wherein the at least one active component is a biological material.
5. The process of claim 4, wherein the biological material is selected from the group consisting of: a protein, a peptide, live cells and a microorganism.
6. The process of claim 1, wherein the at least one active component is selected from the group consisting of: an anti-cancer agent, an anti-inflammatory agent, a hemolytic agent, an anti-diabetic agent, an anti-allergy agent and an anti-fungal agent.

7. The process of claim 1, wherein the at least one active component is a cytokine.

8. The process of claim 1, wherein the at least one active component is selected from the group consisting of: an interleukin, an interferon, EPO, Exenatide, G-CSF, human growth hormone and thymosine.

9. The process of claim 1, wherein the saccharide is selected from the group consisting of: fructose, glucose, invert sugar, lactitol, lactose, maltitol, maltose, sorbitol, sucrose, trehalose, mannitol and combinations thereof.

10. The process of claim 1, wherein the one or more water-soluble gel-forming compounds are selected from the group consisting of: acrylate and derivatives thereof, albumin, alginates, carbomers, carrageenan, cellulose and derivatives thereof, dextran, dextrose, dextrin, gelatin, polyvinylpyrrolidone, starch, pregel starch and combinations thereof.

11. The process of claim 1, wherein the particles are fluidised in the processing chamber and dried by application of heat thereto prior to step (iii).

12. The process of claim 1, wherein in step (iii) the particles rotate.

13. The process of claim 1, wherein step (iii) is performed by introducing an upward moving rotating gas flow into the processing chamber thereby causing the particles to move in an upward direction in a helical path.

14. The process of claim 13, wherein step (iii) is performed by drawing gas through a guide member located at the bottom of, or adjacent to the bottom of, the processing chamber, where upon exiting the guide member the gas moves upwards in a rotating path thereby causing the particles to move in an upward direction in a helical path.

15. The process of claim 14, wherein the guide member comprises an inlet into which a gas is drawn and an outlet from which the gas is discharged, the guide member comprising a gas directing element which acts on the gas passing between the inlet and the outlet such that gas discharged from the outlet moves upward in a rotating path.

16. The process of claim 14, wherein the guide member comprises at least two members which are adapted to rotate about a common axis, wherein a first member includes an inlet into which a gas is able to be drawn and wherein a second member includes one or more gas directing elements which project outwardly from a surface of the second member, wherein the second member is located above the first member and wherein in use gas drawn into the inlet acts on the one or more gas directing elements causing the second member to rotate such that gas discharged from the guide member moves in an upwards direction in a rotating path.

17. The process of claim 13, wherein the gas is at a temperature between about 30° C. and 45° C. when entering the processing chamber.

18. The process of claim 1, wherein prior to commencement of step (iii) or step (iv) air in the processing chamber is replaced with an inert gas.

19. The process of claim 1, wherein step (iv) comprises spraying the coating liquid from the bottom of the processing chamber toward the particles.

20. The process of claim 1, wherein step (iv) comprises spraying the coating liquid in an upwards direction such that the coating liquid moves along a column created by flow of the particles.

21. The process of claim 1, wherein step (iv) comprises spraying the coating liquid in an upwards direction towards the particles at an angle of between about 10° and 70°.

22. The process of claim 1, wherein in step (iv) the coating liquid is at a temperature between about 15° C. and 45° C.

23. The process of claim 1, wherein the coating liquid is in the form of microdroplets prior to contacting the particles.

24. The process of claim 1, wherein the coating liquid is converted into a solid state on the particles within one second of entering the processing chamber.

25. The process of claim 1, wherein steps (iv) and (v) are performed under equilibrium conditions.

26. The process of claim 1, wherein the particles are microparticles.

27. The process of claim 1, for stabilising the at least one active component.

28. The process of claim 1, for preparing sustained release dosage forms.

* * * * *